United States Patent [19]
Höfling

[11] Patent Number: 5,354,279
[45] Date of Patent: Oct. 11, 1994

[54] PLURAL NEEDLE INJECTION CATHETER

[75] Inventor: Berthold Höfling, Wessling, Fed. Rep. of Germany

[73] Assignee: Bavaria Medizin Technologie GmbH, Wessling/Oberpfaffenhofen, Fed. Rep. of Germany

[21] Appl. No.: 132,876

[22] Filed: Oct. 7, 1993

[30] Foreign Application Priority Data

Oct. 21, 1992 [DE] Fed. Rep. of Germany ....... 4235506

[51] Int. Cl.⁵ .................. A61M 5/178; A61M 5/00
[52] U.S. Cl. ..................... 604/164; 604/96; 604/173
[58] Field of Search ............ 604/53, 93, 110, 117, 604/164–168, 174, 192, 198, 256, 264, 272, 283, 95, 96, 102, 106, 107, 115, 130, 156, 173, 175, 181, 239, 258, 281; 606/7, 68, 108, 186, 192–198

[56] References Cited

U.S. PATENT DOCUMENTS

| | | | |
|---|---|---|---|
| 3,570,498 | 3/1971 | Weig | 604/165 |
| 4,136,695 | 1/1979 | Dafoe | 604/165 |
| 4,511,356 | 4/1985 | Froning et al. | 604/198 |
| 4,578,061 | 3/1986 | Lemelson | 604/164 |
| 4,684,369 | 8/1987 | Wildemeersch | 604/272 |
| 4,769,005 | 9/1988 | Ginsburg et al. | 604/53 |
| 4,771,777 | 9/1988 | Horzewski et al. | 606/194 |
| 4,846,785 | 7/1987 | Cassou et al. | 7/1989 |
| 4,861,336 | 8/1989 | Helzel | 604/53 |
| 4,946,442 | 8/1990 | Sanagi | 604/164 |
| 5,088,979 | 2/1992 | Filipi et al. | 604/26 |

FOREIGN PATENT DOCUMENTS

| | | | |
|---|---|---|---|
| 3165781 | 7/1991 | Japan | 604/96 |
| 9210142 | 6/1992 | PCT Int'l Appl. | |

*Primary Examiner*—C. Fred Rosenbaum
*Assistant Examiner*—Mark Bockelman
*Attorney, Agent, or Firm*—Klaus J. Bach

[57] ABSTRACT

A catheter for the injection of a fluid, for example, medicine, into body cavities such as veins or other hollow organs is provided with a head which is insertable into the body cavity and includes hollow needles movably disposed therein between retracted and extended positions and with an operating mechanism mounted to the end of the catheter opposite the head and operatively connected to the needles for moving their front ends outwardly in contact with the walls of the body cavity for supplying the fluid or medicine through the hollow needles directly to the wall portions of the body cavities to be treated. A balloon may be disposed in front of the catheter head and may be inflated or deflated by way of a passage extending through the catheter.

16 Claims, 6 Drawing Sheets

PLURAL NEEDLE INJECTION CATHETER

BACKGROUND OF THE INVENTION

The invention relates to a catheter for the injection of medicine or other fluid into the walls of a hollow organ or another body cavity.

For the medical treatment of patients it is advantageous to utilize treatment methods by which the medicine can be directly applied to the particular infected or ill body part. for treatment, for example, within hollow organs, body cavities, or blood vessels, particularly arteries, various catheters have been proposed by which medicines can be supplied to the area adjacent the tissue to be treated. The most simple catheters of this type are infusion catheters which have one or more openings adjacent the front end of the catheter or which are even perforated. They are expanded so as to come into firm contact with the vessel walls and to supply thereby the medicine directly to the tissue to be treated. In this way an angioplastic balloon (porous balloon) can be provided which has a number of small holes and is expanded upon admission of the medicine under pressure and which thereby is placed into firm contact with the wall of the artery in which it is disposed so that medicine can be supplied to the adjacent tissue under pressure.

It is however a disadvantage of such systems that the medicine is effective only for short periods and the amount of medicine applied is uncertain. If simple infusion catheters are used the medicine may also be carried away very rapidly. It may therefore be necessary to extend the infusion treatment over several days to achieve a hypothetical medicine concentration at the location to be treated. This requires a relatively long hospital stay and also increases the risk of infections or other complications. It is also a disadvantage that the treatment cannot be performed concurrently with a dilatation procedure in a single operation.

It is the object of the present invention to provide a catheter by which, without encountering the above-described disadvantages, medicine can be administered internally in a simple and safe manner particularly directly to the walls of body cavities, hollow organs or vessels where the medicine is needed.

SUMMARY OF THE INVENTION

A catheter for the injection of a fluid, for example, medicine, into body cavities such as veins or other hollow organs is provided with a head which is insertable into the body cavity and includes hollow needles movably disposed therein between retracted and extended positions and with an operating mechanism mounted to the end or the catheter opposite the head and operatively connected to the needles for moving their front ends outwardly in contact with the walls of the body cavity for supplying the fluid or medicine through the hollow needles directly to the wall portions of the body cavities to be treated. A balloon may be disposed in front of the catheter head and may be inflated or deflated by way of a passage extending through the catheter.

The needles of the catheter are maintained in a retracted position within an outer shank of the catheter in which position the catheter can be inserted into a hollow organ or into the veins, particularly the arteries. The catheter is also provided with a mechanism by which the needles can be moved out of the catheter. Such movement is initiated and executed when the catheter is in the desired position. During this procedure the needles engage the walls. The needles are hollow with inner channels through which the medicine can be injected into the tissue. Piercing of the vessel walls by the needles causes perforation which however, because of the small size of the needles, is insignificant so that no bleeding injury is caused thereby. The procedure also provides for the possibility to deposit a medicine storage of a given amount of medicine in the tissue.

For moving the needles there may be provided in the catheter an inner hose which is movable in axial direction with respect to the outer shank and on which the needles are mounted in such a manner that they can be moved by the inner hose so as to engage or pierce the vessel wall. It is also possible to mount the needles on a balloon-like shell which can be expanded. Movement of the needles is achieved in this case by pressurizing the shell. It is also possible to provide the needles with extensions together with which they can be displaced in the catheter.

The medicine of fluid is admitted from the end of the catheter which is disposed outside the human body. If it is desired that the medicine does not enter a great distance into the vessel wall the needle points should be arranged in such a manner that the bevel-cut front faces, which engage the vessel walls, pierce the vessel walls only slightly or are disposed parallel to the vessel walls. This is achieved by arranging the needles in such a way that the front faces of the extended needles are as parallel to the catheter axis as possible. In order to insure that the medicine is administered in the preferred manner it is intended that the needles slightly pierce the tissue. Therefore, a line normal to the front face should not be exactly parallel to the needle axis but should deviate therefrom by at least a small angle so that the needles do not only flatly abut the tissue but their front end can become slightly embedded in the tissue.

The force applied during manipulation and the angle will then determine how deep the needle point pierces into the tissue so that a depth-controlled injection into, top example, a vessel wall is possible in a predetermined location. Of course the needle point is to be cut in correspondence with the intended application and it may be, for example, obtuse, rounded or bevelled.

In accordance with a further embodiment of the invention the needles are mechanically pretensioned, that is, they have in their front portion an inherent curvature whereby the needles, when extended by an operating mechanism, curve outwardly toward the vessel wall. If the needles are more flexible such that the pretension is not sufficient to move the needles in the direction of the wall, the front end of the catheter may include needle guides by which the needle is bent over and guided toward the wall in a controlled manner.

In a particular embodiment the operating mechanism is a multi-lumen hose movable in longitudinal direction with respect to the catheter and including several passages extending from the front end of the catheter to its opposite end. Needles which are pretensioned so as to bend when freed are disposed within these passages at the front end of the catheter. By movement of the multi-lumen hose within the catheter shank the needles can be extended longitudinally whereupon, because of their pretensioned state, they bend outwardly toward the vessel wall. for operation of the needles the catheter is provided at its end opposite the front end thereof with a mechanism which consists essentially of two parts: The first part is connected to the outer catheter shank and the second part is connected to the multi-lumen hose. Both parts are spread apart by means of a spring so that, under normal conditions, the needles are contained within the outer shank of the catheter. forcing the two parts together causes the multi-lumen hose to slide forward within the outer shank so that the needles are moved out of the front end of the catheter.

A similar arrangement may be utilized for operation if the needles are to be forced outwardly by a pressurized balloon-like shell wherein the pressure is generated by forcing the two parts of the operating mechanism together.

It is also possible that the needles have tubular extensions disposed in the catheter over its full length and connected at the other end to the operating mechanism by which the needles are movable longitudinally in the catheter for causing the needles to slide out of the front end of the catheter. Medicine can then be introduced under pressure into the needle extensions within the operating mechanism.

In a further embodiment of the invention a balloon of the type generally in use is disposed directly in front of the injection head of the catheter wherein a lead wire is disposed outside the catheter and extends through an inner lumen (mororail) only in the area of the balloon as shown in U.S. Pat. No. 5,154,725. But it is of course also possible to use a lead wire which extends through the whole catheter shank, the injection head and the balloon.

With such an arrangement treatment of the tissue by medicine can be combined in an advantageous manner with the dilatation procedure to a single operation so that no catheter exchange is required which greatly reduces the time period for the procedure and also the stress for the patient. Furthermore such a combined injection-balloon catheter gives the physician the possibility to make a decision as to the kind of treatment when the catheter is already inserted into the vessel. It is further considered to be advantageous that arranging the balloon in front of the injection head provides for a very smooth widening of the passage. After the injection procedure an additional balloon dilatation can be initiated if this is considered to be advisable for optimizing distribution of the medicine and to smooth out possible mechanical alterations caused by the catheter. Finally, treatment with only a single injection-balloon catheter is more cost effective than treatment with two separate catheters for the same purpose.

BRIEF DESCRIPTION OF THE DRAWINGS

Additional features and advantages of the invention will be apparent from the following description of embodiments thereof in connection with the claims and the drawings:

DESCRIPTION OF THE PREFERRED EMBODIMENTS

Figure 1:
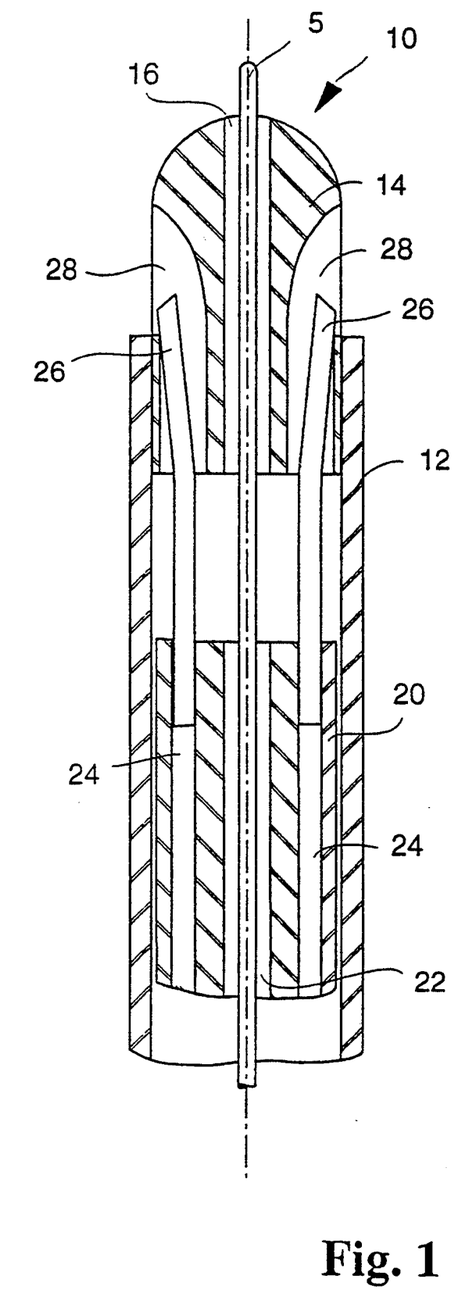
FIG. 1 is a schematic representation of the catheter according to the invention with the needles in their retracted position.

FIG. 1 shows a catheter 10 which may be inserted into a body on a lead wire in a well-known manner. The catheter includes an outer shank 12 at whose end a catheter head 14 is mounted. The catheter head 14 can be firmly connected to the outer shank 12 by welding or cementing. The catheter head 14 includes a longitudinally extending passage 16 receiving a lead wire 5. Further, an inner hose 20 is disposed within the outer shank 12 so as to be longitudinally movable therein. The hose has a central passage 22 in which the lead wire 5 is disposed. The hose is further provided with passages 24 (lumina) with hollow needles 26 mounted thereon at the front end of the catheter. The catheter head 14 includes longitudinal grooves or recesses of a suitable shape (see FIG. 11) which terminate in openings 28 at the side of the catheter head or in the rounded or conical front end of the catheter head.

The hollow needles 26 are pre-bent so that, in the passage 24, they are maintained under a mechanical stress which presses them outwardly onto the outer shank 12. They are prevented from pivoting by side engagement with the groove walls of the opening 28. By sliding the inner hose 20 forwardly within the outer shank 12 the needles are moved forward and, as a result of their pre-bent condition, extend outwardly for engagement with the adjacent vessel wall or they may even pierce the vessel wall so as to reach the adventitia depending on how the operator, based on his experience, operates the device. It is also possible to forcefully bend the needles outwardly by moving them along the inner wall of the openings 28. After the needles 26 are extended a medicine can be supplied to the tissue through the passage 24 and the needle channel which is not shown in the drawings. The medicine is emitted from the end faces 30 of the needles 26. The end faces 30 of the needles are preferably so arranged that, in longitudinal direction, they extend parallel to the catheter axis. This means that the area 30 abuts the vessel wall flatly and can be inserted into the tissue only by application of an increased force. If it is desirable to have the needles enter the tissue, it is advisable to provide a needle end face which is not parallel to the catheter axis such that piercing of the tissue by the needle is facilitated. It is of course possible to use other needle front face cuts, depending on a particular application, to achieve greater tissue penetration. In the embodiment according to FIGS. 1 and 2 several needles 26 are provided and arranged such that they project from the catheter 10 concurrently at several sides of the catheter 10 by forward sliding of the inner hose 20 such that the catheter is supported on the vessel wall from all sides and is centrically supported. Then the surfaces 30 clearly engage the wall or the needles pierce the wall of the tissue if they are cut for that purpose and the unintended washing away of the medicine is prevented. Also, good contact of the end race 30 with the vessel wall is achieved.

Figure 2:
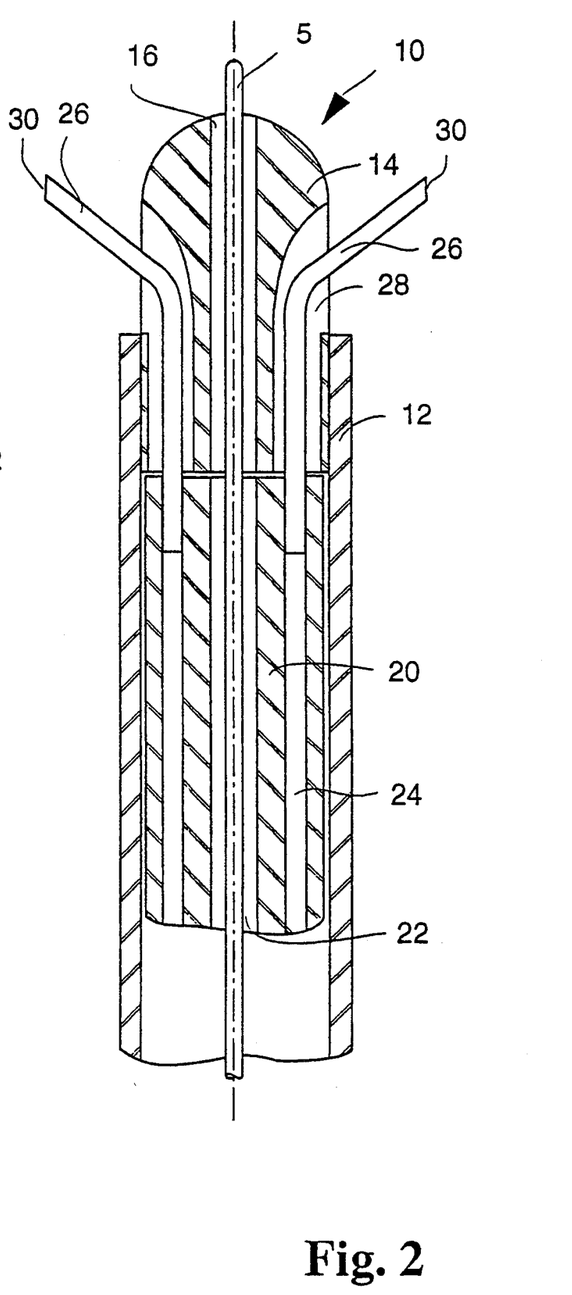
FIG. 2 shows the catheter of FIG. 1 with the needles extended.

In order to provide good support at least three needles should be utilized. However any number of needles may be used and they can be evenly or unevenly distributed over the cross-section of the head. With a larger number of needles also the amount of medicine admitted through the needles can be increased. With very narrow vessels or veins however there may not be sufficient space for a large catheter. Then also only a single needle may be used.

Figure 3:
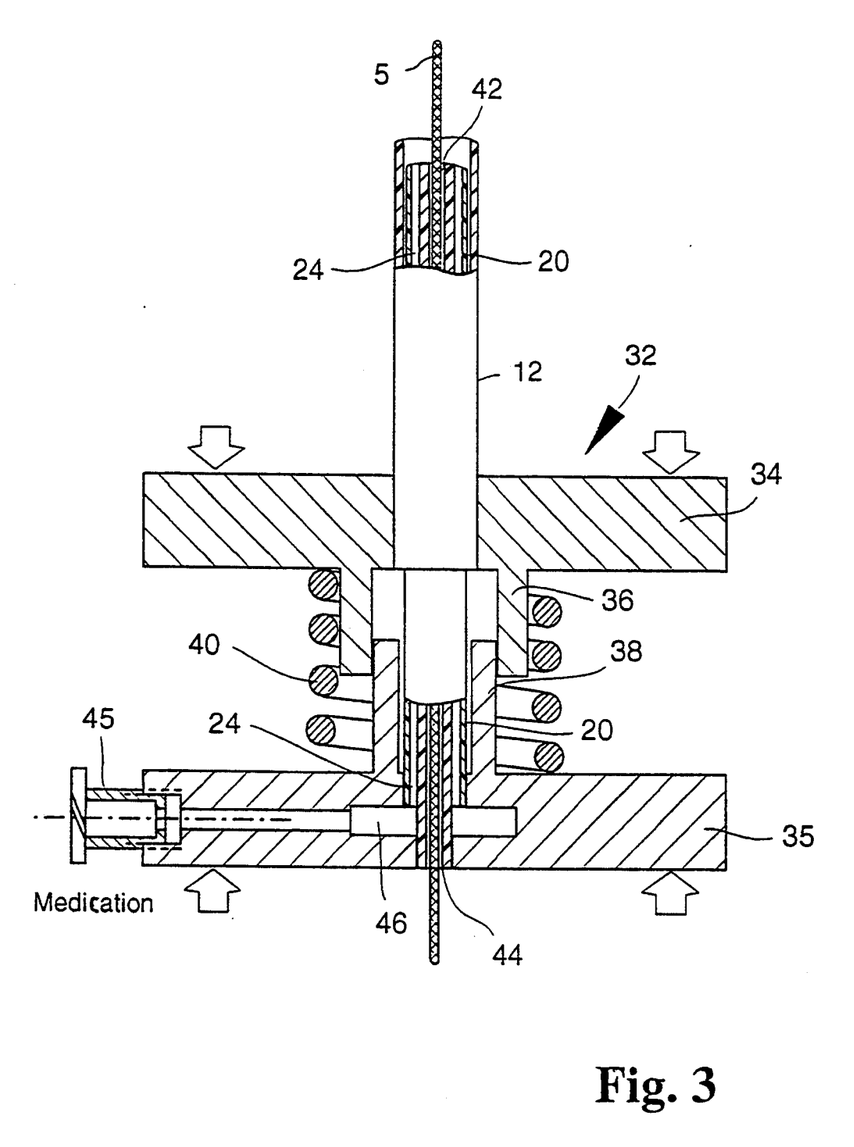
FIG. 3 shows an operating mechanism for moving a multi-lumen hose within the catheter.

If several needles are required because of the greater stability and the possibility to introduce a greater amount of medicine, the inner hose 20 is preferably a multi-lumen hose, FIG. 3 shows an operating mechanism 32 usable for the catheter of FIGS. 1 and 2 for the movement of the needles within a catheter. This operating mechanism consists essentially of two parts 34 and 35. The part 34 is fixed relative to the catheter and will therefore be called stationary part 34. Opposite therefrom there is a movable part 35. The outer shank 12 is firmly connected to the stationary part 34 and the inner hose 20 is connected to the movable part 35. Guide structures 36 and 38 on the stationary and movable parts 34, 35 cooperate with one another in such a way that the inner hose 20 can be moved only axially within the outer shank 12. Both parts 34 and 35 are biased apart by a spring 40. The distance of the front end of the guide structure 38 from the oppositely disposed stop is so chosen that the needles 26 are normally in the retracted position as shown in FIG. 1. If the movable part 35 is moved toward the stationary part 34, the inner hose is moved toward the front end of the catheter until the position according to FIG. 2 is achieved in which the needles engage the vessel walls as a result of their pre-bent state.

FIG. 3 shows that the inner hose 20 is connected to the movable part 35 while the inner lumen 42 continues through the back of the part 35 where it has an opening 44 through which the lead wire 5 extends. The medicine is supplied by way of a side socket 45 to a distribution chamber 46 and then via passages 24 to the needles 26.

Figure 4:
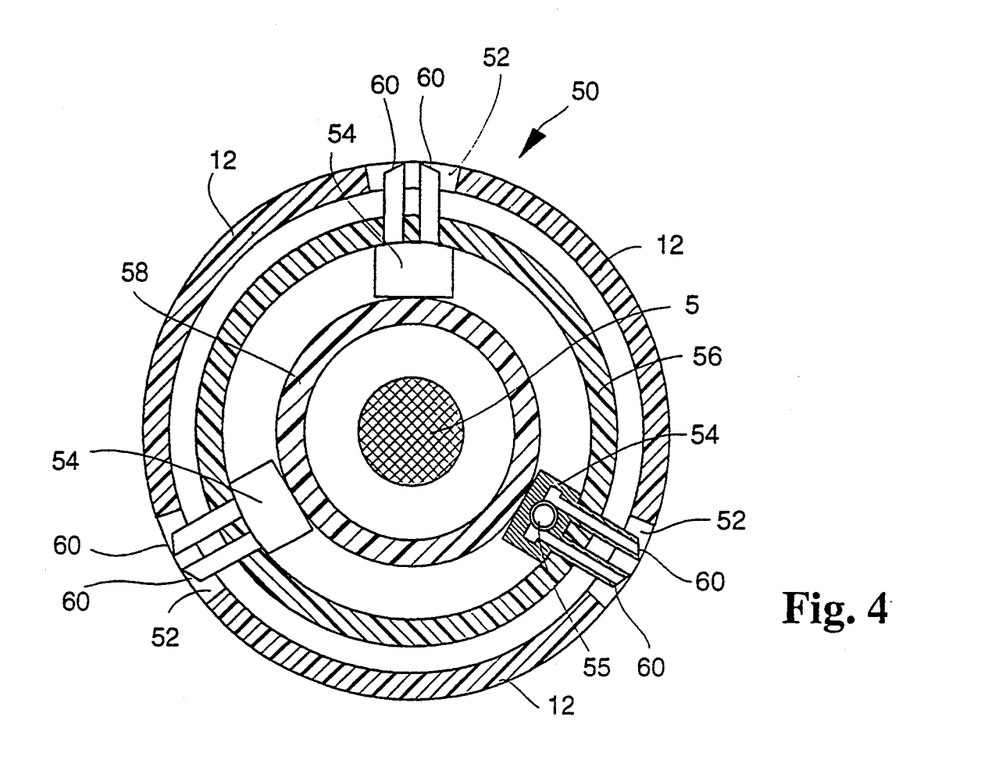
FIG. 4 is a radial cross-sectional view of another embodiment of the invention.

FIG. 4 is a cross-sectional view of another embodiment of the catheter. This catheter 50 includes an outer shank 12 and a lead wire 5 in the center of the catheter. The outer shank 12 has holes 52 through which needles 54 can be moved outwardly from within the catheter.

The needles 54 are mounted on an inner hose 56. Between the inner hose 56 and the lead wire 5 there is an additional hose 58 which is so elastic that it can be expanded balloon-like when pressurized fluid is admitted to the space between hose 56 and hose 58 until the hose 56 abuts the outer shank 12. This expansion moves the needles 54 outwardly through the holes 52 so as to engage or even pierce the surrounding vessel walls. In the shown example the needle points are formed different from those shown in FIGS. 1 and 2. They have an end face which is not parallel to the catheter axis so that the needle points can penetrate deeper into the vessel wall or the adjacent tissue. The advantages of such an arrangement have been given earlier. But it would certainly be possible to provide the needles 54 with front faces 60 which, like the front faces 30 of the first embodiment, flatly bear against the vessel wall.

In the embodiment of FIG. 4 medicine is supplied to the needles through separate passages connected to the bores 55 in the needle bases and the hollow space between the hoses 56 and 58 is pressurized independently. This avoids a substantial disadvantage of balloon-like inflatable catheters as presently known because, even with high inflation pressure, the medicine can be administered, for example, under low pressure. Furthermore, the individually selectable movability of the needles which results in different needle penetrations permits different placement of the medicine, for example, into the inner layers of the vessel, the vessel wall or for storage in the area of the vessel. In addition, it is advantageous that dilatation and medicine injection can be treated as two clearly separate procedures which can be individually controlled. for this purpose, an operating mechanism of the well-known type can be used by which the pressure fluid and the medicine are supplied separately.

With such a mechanism for operating the catheter 50 the inflation pressure for expanding the inner hose 56 is admitted to the space between the two hoses 56 and 58 so that dilitation can be performed independently. The medicine is supplied to the passages in the space between the needles which are connected to the needles via a separate connector of the operating mechanism. Both embodiments have the advantage that the use of needles 26 or 54 provides for an accurately controllable administration of medicine to a particular area of the vessel wall. The use of needles with front end faces of particular shapes also provides for some control of the piercing depths of the needles and the delivery depth for the medicine into the surrounding tissue.

Figure 5:
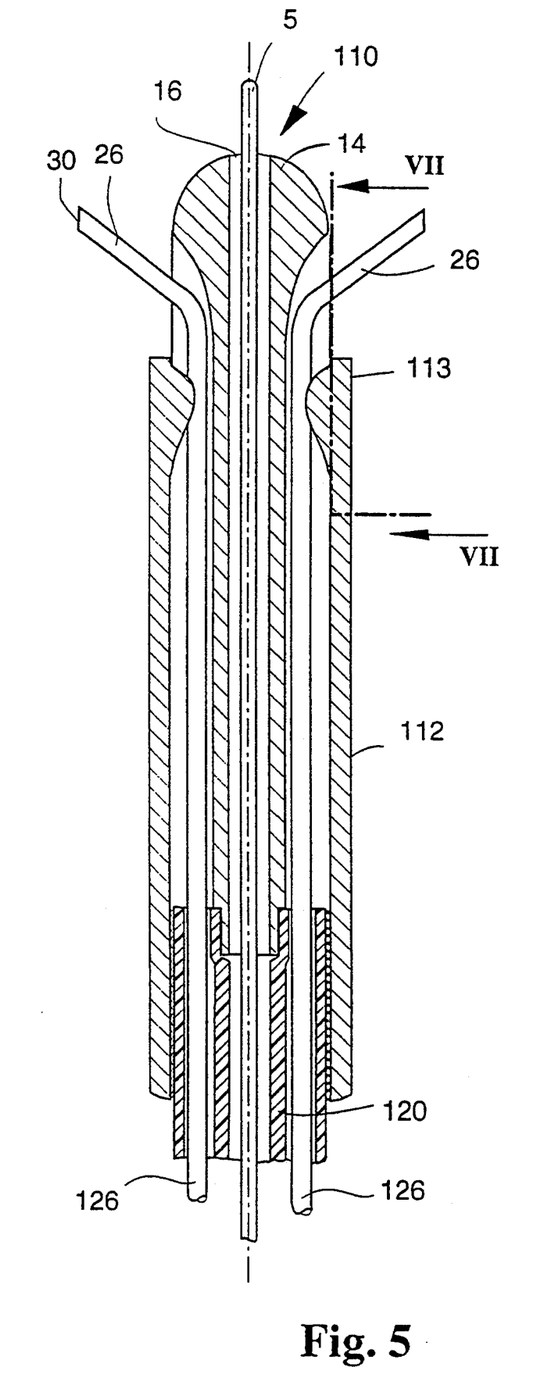
FIG. 5 shows another embodiment of the catheter according to the invention.

FIG. 5 shows another embodiment of a catheter 110 wherein elastically outwardly pre-bent needles 26 have tubular extensions 126 which may be formed integral with the needles and which extend through the passages of a multi-lumen hose catheter which passages are large enough to permit longitudinal movement of the extensions therein.

Figure 6:
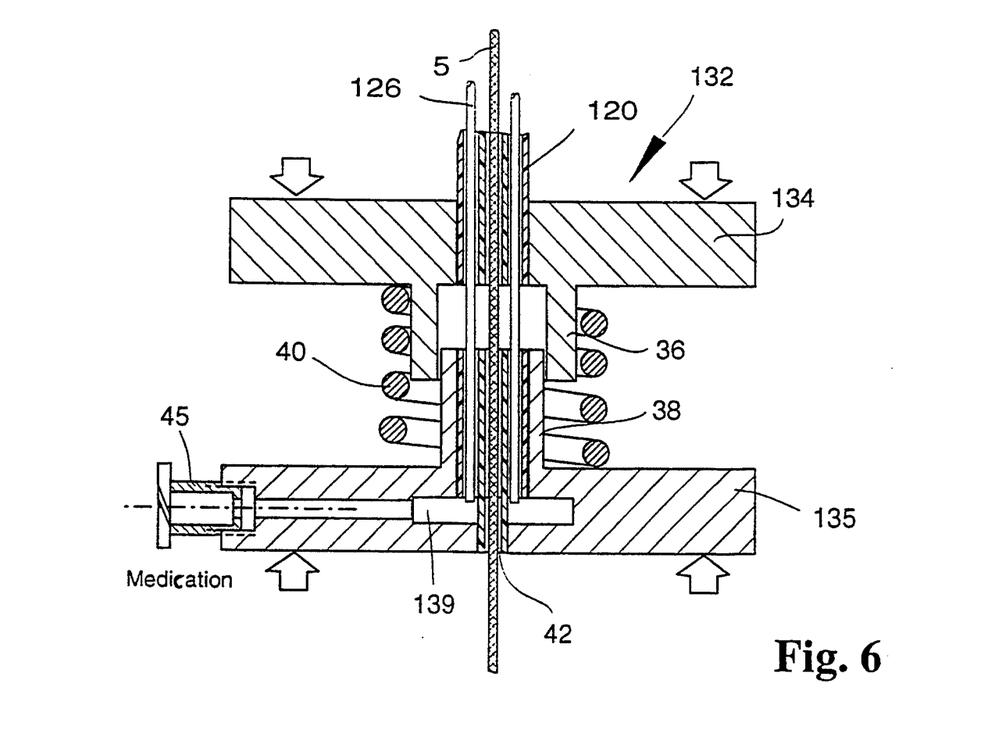
FIG. 6 shows an operating mechanism for moving the needles in the catheter according to FIG. 5.
Figure 7:
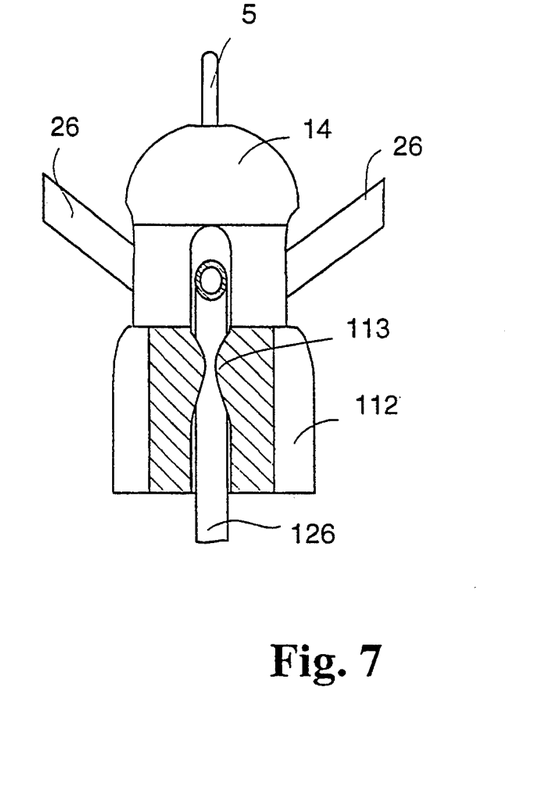
FIG. 7 is an enlarged cross-sectional view along line VII—VII of FIG. 5.

Attached to the front end of the multi-lumen hose is an outer shank 112 in which the needles are guided and into which they can be retracted. The catheter front end 14 cooperating with the outer shank 112 is, as mentioned earlier, shaped in such a way that the elastically pre-bent needles 26 are appropriately guided when extended. In accordance with FIGS. 5 and 7 the outer shank 112 may have projections 113 for engaging and guiding the needles in addition to the guidance provided by the groove-like openings 28 for preventing pivoting of the needles when they are extended. The guide rod 5 extends through the front end of the catheter in the normal manner. Preferably the front end of the catheter and the outer shank consist of metal or a hard, easily slidable plastic material.

for axially moving the needles 26 with their extensions 126 the operating mechanism 132 as shown in FIG. 6 is utilized. Essentially, it corresponds to the operating mechanism shown in FIG. 3. The rear end of the multi-lumen hose 120 is connected to the stationary part 134 whereas the needle extensions 126 extend to the movable part 135 and are mounted there in such a way that fluid or medicine can be supplied under pressure from the distribution cavity 139 to the needle extensions 126. Operation of the operating mechanism is as described in connection with FIG. 3. The mechanism is shaped so as to be operable by one hand.

There may be an even number or an uneven number of needles and they may be evenly or unevenly distributed over the catheter cross-section.

It is also possible that, with the use of, for example, two needles, the lead wire 5 is disposed off-center, for example, in a third passage of the multi-lumen hose. In this case, the lead wire may also project from the front end of the catheter off-center.

A catheter of the type described has preferably a diameter of between 0.5 to 5 mm with a catheter head length of 1 mm to 10 mm.

Figure 8:
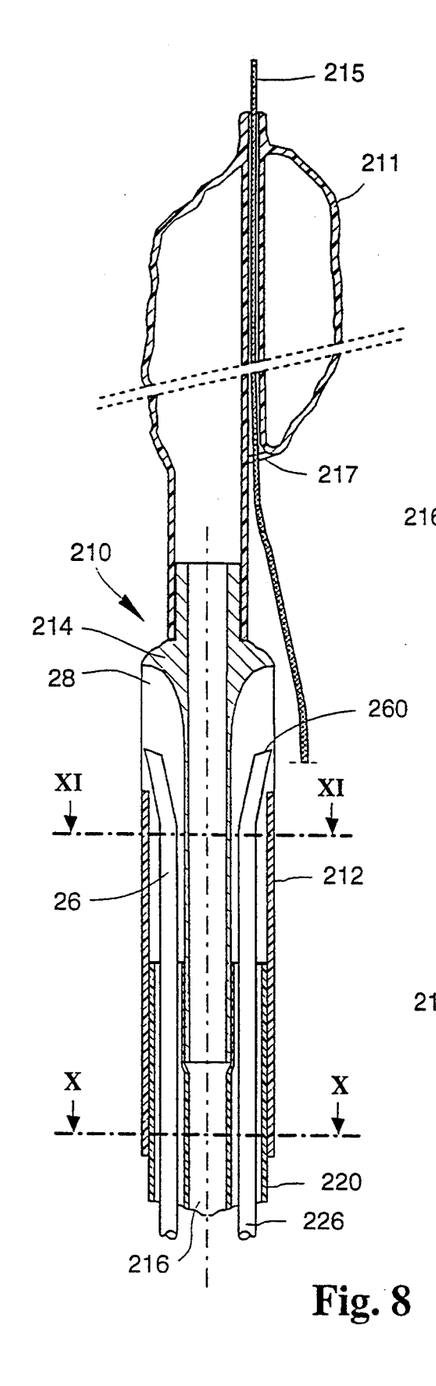
FIG. 8 is a cross-sectional view of a head portion of a combined injection-balloon catheter taken along line VIII—VIII of FIG. 11.

FIG. 8 shows another embodiment of the invention wherein a balloon 211 is arranged in front of the injection head 210. In this case, the lead wire extends only through the interior of the balloon as it is common with the so-called monorail catheters. The front end 214 of the injection head corresponds essentially to the arrangement according to FIG. 5 wherein the catheter front end 214 is connected to the multi-lumen hose 220 by means of an outer shank 212. The hollow needles 26 extend from the catheter head 214 through the multi-lumen hose 220 up to the operating mechanism of FIG. 9 where the needles are connected to the operating mechanism as described below.

The fluid for the inflation is supplied through the inner lumen 216 of the multi-lumen hose 220 which inner lumen extends as a passage through the catheter head 214 and terminates in the lumen for the inflation of the balloon 211.

Figure 10:
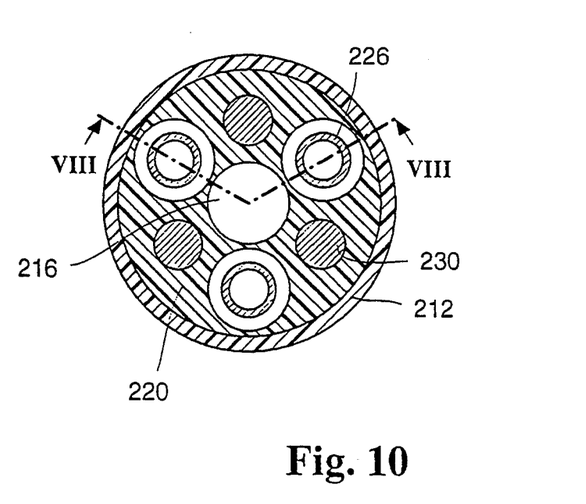
FIG. 10 is a cross-sectional view along line X—X of FIG. 8.
Figure 11:
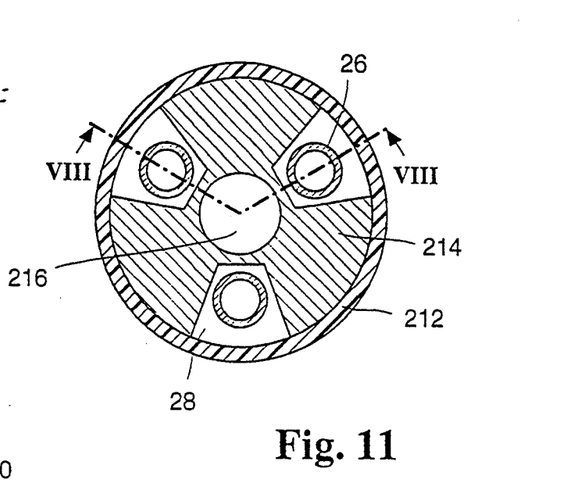
FIG. 11 is a cross-sectional view along line XI—XI of FIG. 8.

FIGS. 10 and 11 are two cross-sectional views of the catheter head wherein FIG. 10 shows a multi-lumen hose 220 which is surrounded by an outer shank 212 in which the passages for the hollow needles and their extensions 226 are disposed relative to one another in a triangular array. Reinforcement wires 230 are disposed between the passages for the needle extensions and are molded into the multi-lumen hose material. They insure that the catheter will not kink sidewardly during movement of the needles in the catheter.

Figure 9:
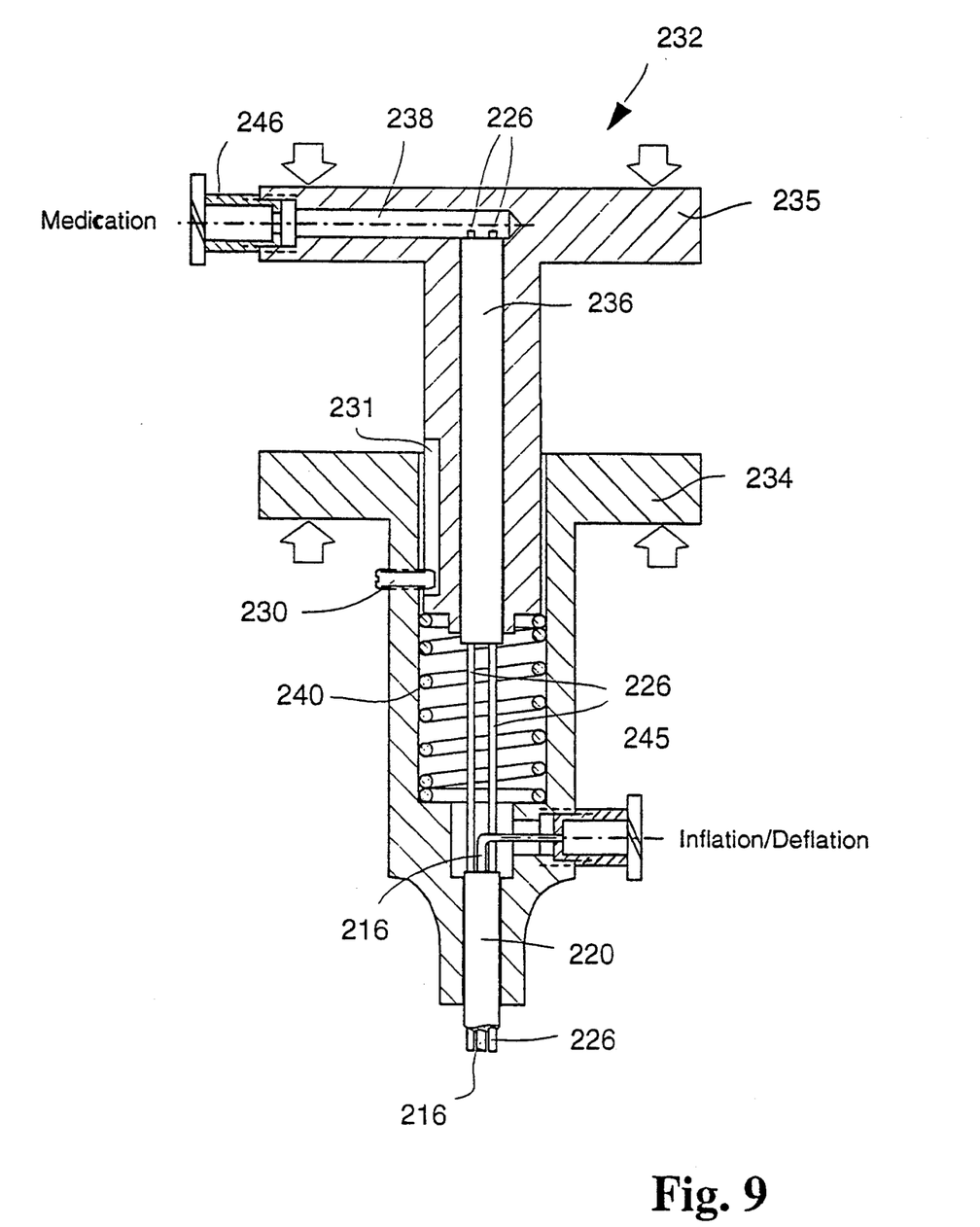
FIG. 9 shows the operating mechanism for longitudinally moving the injection needles in a catheter with connection for the medicine and for inflation/deflation of the balloon.

FIG. 9 shows how the operating mechanism 232 facilitates slidingly moving the needles, that is, their extensions 226, through the multi-lumen hose 220 for the injection of medicine. Again the operating mechanism includes a stationary part 234 and a movable part 235 which, by means of a spring 240, are maintained spaced from one another in which position the hollow needles are retracted into the catheter head 214. The travel length, that is, the distance by which the needles can be extended from the catheter head, is determined by the stop pin 230 which is mounted in the stationary part 234 and which is received in a groove 231 in the movable part 235. The length of the groove 231 determines the needle travel distance.

The multi-lumen hose 220 is cemented into the front end of the stationary part 234 so as to be firmly retained therein. Correspondingly, the section 236 of a multi-lumen hose is firmly mounted in the movable part 235 through which the ends of the needle extensions 226 extend to the distribution chamber 238 and into which they are cemented for movement therewith. This permits movement of the needles and of the catheter head when the operating mechanism is operated as indicated by the arrows.

The inner lumen 216 is bent outwardly in the stationary part 234 and terminates in a connector 245 through which the fluid for the inflation of the balloon is supplied in the known manner. Via the same connection also deflation of the balloon is achieved.

The movable part 235 includes a corresponding connector 246 which provides for communication with the distribution chamber 238 and through which medicine is supplied in the usual manner.

In order to facilitate understanding, some figures show the components enlarged for better recognition of the features of the invention.

What is claimed is:

1. A catheter for the injection of a fluid, such as a medicine, into body cavities such as veins or hollow organs, comprising: a catheter head with a catheter shank having a longitudinal axis and being insertable into said body cavity through an insertion passage, a plurality of needles distributed in a predetermined pattern around, and disposed in, the catheter head movably between a retracted position in which the needles are disposed within the catheter head and an extended position in which the front ends of the needles project from the catheter head through openings formed therein, said needles being mounted on a multi-lumen hose which is longitudinally movably supported within the catheter, said catheter being provided at its end opposite the catheter head with an operating mechanism including two spaced relatively movable parts, said catheter shank being connected to one part of said operating mechanism and said multi-lumen hose with a plurality of with a plurality of individual passages being connected to the other part, said parts being held in spaced relationship by a spring opposing their compression, said multi-lumen hose moving the needles connected thereto from their retracted positions to their extended positions upon compression of the two parts against the force applied by said spring, said needles being hollow so as to form needle passages and being in communication with the individual passages in said multilumen hose, said other part including a distribution chamber in communication with said individual passages and connected to means for supplying said fluid or medicine for transmitting it to said needles for injection into the walls of said cavity.

2. A catheter according to claim 1, wherein said needles have tubular extensions disposed in the catheter, said tubular extensions being connected to a supply of fluid or medicine for admitting it to said needles.

3. A catheter according to claim 1, wherein the needles are arranged around the catheter head at evenly spaced intervals of 120°.

4. A catheter according to claim 1, wherein said needles have front faces, which, in the extended positions of the needles, are parallel to the catheter axis.

5. A catheter according to claim 1, wherein said needles have front faces which, in the extended positions of the needles, are disposed at an angle with regard to the catheter axis.

6. A catheter according to claim 1, wherein sold needles have pre-bent end portions which are held in said catheter short under tension so that, upon forward movement of the needles, they bend outwardly through openings in the catheter head.

7. A catheter according to claim 6, wherein said catheter head includes a needle guide structure for holding said needles in proper orientation and guiding them through the openings in said catheter head.

8. A catheter according to claim 1, wherein a balloon is disposed in front of the catheter head and is in communication with one passage in the multi-lumen hoses for inflation and deflation of said balloon.

9. A catheter according to claim 1, wherein a lead wire extends through said multi-lumen hose and through said catheter head for guiding the catheter upon insertion into said body cavities.

10. A catheter for the injection of a fluid, such as a medicine, into body cavities such as veins or hollow organs, comprising: a catheter head with a catheter shank insertable into said body cavity through an insertion passage, a plurality of needles distributed in a predetermined pattern around, and disposed in, the catheter shank movably between a retracted position in which the needles are disposed within the catheter shank and an extended position in which the front ends of the needles project from the catheter shank out the catheter head, said needles having extensions movably received in a multi-lumen hose which has a plurality of individual passages receiving individual needle extensions and which is disposed in said catheter shank, an operating mechanism mounted to the end of said catheter opposite the catheter hose and including two spaced relatively movable parts, said multi-lumen hose being connected to one part of said operating mechanism and said needle extensions being connected to the other part of said operating mechanism, said parts being held in spaced relationship by a spring opposing their compression, said needle extensions being moved in said multi-lumen hose passages upon compression of said two parts against the force of said spring so as to move said needles from their retracted positions to their outwardly extended positions, said needles and said needle extensions being hollow and being connected to said other part of said operating mechanism, said other part including a distribution chamber in communication with said hollow needle extensions and connected to means for supplying said fluid or medicine thereto for transmitting it to said needles for injection of said fluid or medicine into the walls of said cavity.

11. A catheter according to claim 10, wherein a balloon is disposed in front of the catheter head and is in communication with one passage in the multi-lumen hose for inflation and deflation of said balloon.

12. A catheter according to claim 10, wherein a lead wire extends through said multi-lumen hose and through said catheter for guiding the catheter upon insertion into said body cavities.

13. A catheter according to claim 10, wherein a balloon is disposed in front of the catheter head and is in communication with one passage of the multi-lumen hose for inflation and deflation of said balloon and a lead wire extends through said balloon for guiding said catheter upon insertion into said body cavities.

14. A catheter according to claim 13, wherein said lead wire extends through said catheter head and said multi-lumen hose.

15. A catheter for the injection of a fluid, such as a medicine, into body cavities such as veins or hollow organs, comprising: a catheter head with a catheter shank insertable into said body cavity through an insertion passage, a plurality of needles distributed in a predetermined pattern around, and disposed in, the catheter head and being movable between a retracted position in which the needles are disposed within the catheter head and an extended position in which the front ends of the needles project from the catheter head through openings formed therein, said needles being mounted on an inner hose, an additional hose disposed within said inner hose defining a sealed passageway, means for supplying pressurized fluid to said passageway for expanding the inner hose and for forcing the inner hose outwardly for outward movement of the needles through the openings in the catheter head, said needles being supplied with an injection fluid by passages provided within said inner hose.

16. A catheter according to claim 15, wherein a lead wire extends through said additional hose and through said catheter for guiding the catheter upon insertion into said body cavities.

* * * * *